(12) United States Patent
Wittland et al.

(10) Patent No.: US 10,576,217 B2
(45) Date of Patent: Mar. 3, 2020

(54) SAFETY DEVICE FOR A SYRINGE

(71) Applicants: Gerresheimer Regensburg GmbH, Regensburg (DE); Gerresheimer Bunde GmbH, Bunde (DE)

(72) Inventors: Frank Wittland, Enger (DE); Maximilian Vogl, Mantel (DE)

(73) Assignees: Gerresheimer Regensburg GMBH, Regensburg (DE); Gerresheimer Bunde GMBH, Bunde (DE)

( * ) Notice: Subject to any disclaimer, the term of this patent is extended or adjusted under 35 U.S.C. 154(b) by 127 days.

(21) Appl. No.: 15/573,052

(22) PCT Filed: Jun. 28, 2016

(86) PCT No.: PCT/EP2016/064909
§ 371 (c)(1),
(2) Date: Nov. 9, 2017

(87) PCT Pub. No.: WO2017/012833
PCT Pub. Date: Jan. 26, 2017

(65) Prior Publication Data
US 2018/0110934 A1  Apr. 26, 2018

(30) Foreign Application Priority Data

Jul. 21, 2015  (DE) .................. 10 2015 111 840

(51) Int. Cl.
*A61M 5/32* (2006.01)
*A61M 5/31* (2006.01)

(52) U.S. Cl.
CPC ........ *A61M 5/3204* (2013.01); *A61M 5/3202* (2013.01); *A61M 5/326* (2013.01);
(Continued)

(58) Field of Classification Search
CPC .............. A61M 5/3204; A61M 5/3202; A61M 5/3272; A61M 2005/312
See application file for complete search history.

(56) References Cited

U.S. PATENT DOCUMENTS 7,641,636 B2 * 1/2010 Moesli ................ A61M 5/3202
604/162
2009/0198196 A1 * 8/2009 West .................... A61B 5/1405
604/263

(Continued)

FOREIGN PATENT DOCUMENTS

| DE | 112009001083 T5 | 3/2011 |
|---|---|---|
| WO | WO 2011/039238 A1 | 4/2011 |
| WO | WO 2014/131987 A1 | 9/2014 |

OTHER PUBLICATIONS

International Search Report with Written Opinion corresponding to International Patent Application No. PCT/EP2016/064909, dated Sep. 8, 2016.

(Continued)

*Primary Examiner* — Rebecca E Eisenberg
*Assistant Examiner* — Melissa A Snyder
(74) *Attorney, Agent, or Firm* — Leydig, Voit & Mayer, Ltd.

(57) ABSTRACT

The invention relates to a safety device for a syringe for avoiding stab wounds, said syringe having a syringe body and a piercing means arranged on the distal end of the syringe body. The safety device comprises a sleeve element that extends along an axial direction (X) and at least partially encloses the piercing means and the syringe body, and an inner element which is at least arranged at least in sections inside the sleeve element and surrounds the piercing means. Said safety device is characterised in that the inner element comprises a rim section and a piercing means protection section surrounding the piercing means. Said rim section can (Continued)

be arranged on a distal end of the syringe body, the safety device is secured to the syringe body, and the piercing means protection section can be removed from the rim section before using the syringe.

19 Claims, 4 Drawing Sheets

(52) U.S. Cl.
CPC ..... *A61M 5/3272* (2013.01); *A61M 2005/312* (2013.01); *A61M 2005/3267* (2013.01); *A61M 2205/0216* (2013.01); *A61M 2207/00* (2013.01)

(56) References Cited

U.S. PATENT DOCUMENTS

| | | |
|---|---|---|
| 2011/0137261 A1 | 6/2011 | Garber et al. |
| 2015/0190586 A1 | 7/2015 | Takemoto |
| 2016/0008553 A1 | 1/2016 | Fournier et al. |
| 2018/0104421 A1 | 4/2018 | Wittland et al. |
| 2018/0133409 A1 | 5/2018 | Fraas et al. |
| 2018/0161511 A1 | 6/2018 | Fraas et al. |
| 2018/0161512 A1 | 6/2018 | Wittland et al. |
| 2018/0161516 A1 | 6/2018 | Wittland et al. |

OTHER PUBLICATIONS

U.S. Appl. No. 15/573,048, filed Nov. 9, 2017.
U.S. Appl. No. 15/573,065, filed Nov. 9, 2017.
U.S. Appl. No. 15/573,032, filed Nov. 9, 2017.
U.S. Appl. No. 15/573,047, filed Nov. 9, 2017.
U.S. Appl. No. 15/573,038, filed Nov. 9, 2017.
EP Office Action, dated Nov. 19, 2019, in European Patent Application No. 16 732 316.1, 4 pp.

* cited by examiner

SAFETY DEVICE FOR A SYRINGE

CROSS-REFERENCE TO RELATED APPLICATIONS

This application is a U.S. National Stage Application under 35 U.S.C. § 371 of International Application No. PCT/EP2016/064909, filed Jun. 28, 2016, which claims the benefit and priority of German Patent Application No. 102015111840.8, filed Jul. 21, 2015, both of which are hereby incorporated by reference in their entirety to the extent not inconsistent herewith.

The invention relates to a safety device for a syringe for avoiding stab wounds, said syringe having a syringe body and a piercing means arranged at the distal end of the syringe body, said safety device comprising a sleeve element, which extends in an axial direction (X) and encloses the piercing means and the syringe body at least in part, and an inner element, at least portions of which are arranged inside the sleeve element and encloses the piercing means.

Generic safety devices for avoiding stab wounds are known in the art. The use of such safety devices is expedient in particular in prefilled syringes. Such syringes are very simple to handle, as the medium does not have to be transferred to the syringe prior to use. Furthermore, the probability of administering the wrong drug is very low, even in an emergency. For vaccines and countless other drugs they are now the first-choice primary packaging material. These syringes are usually made of glass or plastics material (for example COC, COP) and have to be provided with protective caps to prevent damage to and/or contamination of the cannula before the syringe is used. In addition, it is important to secure the cannula after use of the syringe so as to prevent stab wounds. Careless replacement of the protective cap on the cannula can result in stab wounds. Often, the protective cap in question can no longer be found, or it is forgotten to put it on again it, resulting in a preventable risk of injury.

Accordingly, needle guards have been developed which are rigidly connected to the syringe and automatically receive the needle again after the syringe has been used. A needle guard of this type is disclosed for example in DE 11 2009 001 083 T5. This document discloses a spring-driven safety sleeve which, when extended, encloses the cannula and ensures that it cannot injure the user. The safety sleeve has a curved path in which at least one guide pin runs, thus allowing for different positions of the safety sleeve depending on the needle tip. The at least one guide pin has to be fastened to the front geometry of the syringe by means of a collar or rigidly connected to the syringe in some other way. To preclude tampering or incorrect use, it must be impossible or only possible with difficulty to remove the collar together with the guide pin from the syringe comprising a cannula. Thus, an appropriately firm fit in the axial direction is required.

In the area of prefilled syringes, before the filling process is even carried out, a safety device for avoiding stab wounds or a protective cap is mounted on the syringe body and sterilised in standard packaging, for example a syringe nest. In this context, the syringes are also referred to as "ready to use" (RTU) or "ready to sterilise" (RTS) syringes. In general, in addition to the safety device, a further needle guard is arranged above the cannula so as to protect the cannula from damage and/or contamination. A needle guard of this type is also known as a rigid needle shield or flexible needle shield. It has thus far been complex to mount generic safety devices comprising an additional needle guard. This results in high production costs and an insufficient number of safety devices being manufactured.

The object of the present invention is to provide a safety device for a syringe for avoiding stab wounds, which allows for simple and cost-effective mounting.

This object is achieved by a safety device for a syringe for avoiding stab wounds, said syringe having a syringe body and a piercing means arranged at the distal end of the syringe body, said safety device comprising a sleeve element, which extends in an axial direction (X) and encloses the piercing means and the syringe body at least in part, and an inner element, at least portions of which are arranged inside the sleeve element and enclose the piercing means. The safety device is further characterised in that the inner element comprises a collar portion and a piercing means protection portion that encloses the piercing means, the collar portion being arrangeable on a distal end region of the syringe body, the safety device being fastened to the syringe body, and the piercing means protection portion being detachable from the collar portion before the syringe is used.

Thus, as a result of the inner element according to the invention, the safety device is fastened to the syringe body and the piercing means is protected from damage and/or contamination. The piercing means may in this case be a cannula, a needle or else a lancet. In the art, a mounting element is usually used for fastening the safety device, and a needle guard is usually used for protecting the piercing means. The inner element according to the invention allows the final mounting of the safety device to proceed in a very simple manner, since merely one element is mounted which performs the function of a mounting element and of a needle guard. In effect, the inner element is an integral or single-piece embodiment of a mounting element and a needle guard. Preferably, the inner element can be mounted merely by way of a pressing movement. This provides a significant advantage over the prior art as regards the efficiency of the mounting process. Before the syringe is used, the piercing means protection portion can be detached from the collar portion, causing the piercing means to be uncovered.

In accordance with a particularly preferred concept of the invention, a predetermined breaking point is arranged between the collar portion and the piercing means protection portion. Before the syringe is used, the predetermined breaking point can be broken apart, for example by means of a rotary or pulling movement, and the piercing means protection portion can be detached from the collar portion.

Preferably, the predetermined breaking point is arranged between a distal end face of the collar portion and a proximal end of the piercing means protection portion. Preferably, the predetermined breaking point is a material taper and/or a perforation and/or a notch and/or a crack in the material. However, other known embodiments of predetermined breaking points are also conceivable.

In accordance with another particularly preferred concept of the invention, the collar portion has at least one guide projection which engages in at least one guide slot of the sleeve element. Preferably, the guide projection is substantially guided in the axial direction (X) in the at least one guide slot of the sleeve element when the syringe body moves relative to the sleeve element. In this case, the safety device is substantially formed as a hollow circular cylinder. When the syringe is used, the syringe with the safety device of the syringe is pressed against the patient's skin. As a result of the movement of the syringe body relative to the sleeve element and the guidance of the guide projection in the guide slot, which has a curved path, the sleeve element is rotated in a circumferential direction (U). As a result, the sleeve element preferably slides over the syringe body, causing the piercing means, which may be a cannula, a needle or a lancet, to pass through a corresponding opening in the sleeve element.

According to a preferred embodiment, the collar portion is arranged on the distal end region of the syringe body such that it can rotate in a circumferential direction (U). Thus, when the syringe is used, the movement of the syringe body relative to the sleeve element and the guidance of the guide projection in the guide slot results in a rotational movement of the collar portion, instead of the sleeve element, in a circumferential direction (U). As a result, the sleeve element preferably slides over the syringe body, causing the piercing means to pass through a corresponding opening in the sleeve element. This prevents rotation of the sleeve element on the patient's skin around the injection site, which would be unpleasant for the patient.

Preferably, the piercing means protection portion has a cavity in a proximal end region. Preferably, the piercing means and portions of the distal end region of the syringe body are arrangeable in the cavity.

Preferably, an inner part made of a resilient material is arranged in the cavity in the piercing means protection portion. In addition, the resilient material is preferably rubber or a synthetic elastomer. Advantageously, the inner part encloses the piercing means in this case. In general, piercing means, for example cannulas, have a very finely polished surface so as to allow for an injection that is as pain-free as possible. This polished surface can easily be damaged by mechanical influences, as a result of which the patient may be caused unnecessary pain during an injection. As a result of the resilient inner part, further protection against mechanical influences is provided. The piercing means thus advantageously abuts the inner walls of the resilient material, resulting in the polished surface being protected in the event of mechanical influences. Furthermore, it would be conceivable for the inner part to sealingly abut the distal end region of the syringe body by a proximal end thereof. The region surrounding the piercing means would thus be tightly sealed. This effectively protects the piercing means against contamination.

In accordance with another advantageous concept of the invention, the collar portion is substantially formed as a hollow circular cylinder. Preferably, the circular cylinder has a lateral surface on which the at least one guide projection is arranged. Preferably, the at least one guide projection extends radially away from the lateral surface. The guide projection is also preferably formed as a circular cylinder or as a pin. Advantageously, two diametrically opposite guide projections are arranged on the lateral surface. Accordingly, the sleeve element would also have two diametrically opposite guide slots, in each of which one guide projection is guided. More preferably, an external diameter of the collar portion is greater than an external diameter of the piercing means protection portion.

Preferably, the syringe body is designed as a hollow circular cylinder and has in the distal end region thereof a conical end piece on which the piercing means is arranged. Preferably, the syringe body consists of glass or a polymeric plastics material, preferably a polyolefin, for example polypropylene or polyethylene, particularly preferably of a cyclic olefin polymer (COP) or of a cyclic olefin copolymer (COC).

More preferably, a projection, on which an end face of the distal end of the collar element can engage, is formed on the conical end piece, making it possible to lock the collar element and thus the safety device in the axial direction. To preclude tampering with or incorrect use of the syringe, it must be impossible or only possible with difficulty to remove the safety device from the syringe comprising a cannula. Thus, an appropriately firm fit in the axial direction is required.

Preferably, the collar portion comprises a distal region and a proximal region. Preferably, in the distal region the wall of the collar portion has at least two slits which extend in the axial direction (X). Slits of this type ensure that the collar portion adapts to different syringe body shapes or syringe body diameters. Furthermore, the slits facilitate the attachment of the inner element to the syringe body. More preferably, the collar portion has an inside taper in the proximal region thereof. As a result of this proximal region, a second bearing point is formed in the region of the syringe shoulders, at which the collar portion bears against the syringe body.

Preferably, the safety device has at least one spring element, which is operatively connected to the syringe body and counteracts the movement of the syringe body relative to the safety device. Thus, the cannula remains inside the sleeve element until the intended use. During use, the sleeve element has to be displaced counter to the spring force in order for the piercing means to be able to pass through the opening in the sleeve element. After the syringe has been used, the sleeve element, driven by the spring force of the spring element, automatically slides back over the piercing means. The user is thus protected from stab wounds from the used, contaminated piercing means. Preferably, the spring element comprises a spiral spring. However, different spring types are also conceivable, such as leg springs or torsion springs. It would also be conceivable to form the spring element as an elastomer.

In a preferred embodiment, the collar portion and the piercing means protection portion are made of different materials. Preferably, the inner element is manufactured by a multi-component injection-moulding method. In a method of this type, the injection-moulding machine used only has one mould having a plurality of injection units. The injection-moulded parts can thus be cost-effectively manufactured in one pass using only one mould. It would also be conceivable for the two portions of the inner element to be manufactured individually and subsequently welded.

Preferably, the piercing means protection portion is made of a thermoplastic elastomer (TPE) and the collar portion is made of polyoxymethylene (POM). POM is used as a technical plastics material, in particular for precision parts, because of the high stiffness, low coefficients of friction, excellent dimensional stability and thermal stability thereof. Thermoplastic elastomers are plastics materials which behave in a similar manner to conventional elastomers at room temperature, but can be plastically deformed when heat is supplied and thus exhibit thermoplastic behaviour.

In a further aspect, the object of the invention is also achieved by a method for mounting the safety device according to any of the preceding claims and for arranging the safety device on a syringe body using the following method steps:

a) inserting the spring element into the interior of the sleeve element in the axial direction (X);

b) inserting the inner element into the interior of the sleeve element in the axial direction (X) such that the spring element is arranged between the collar portion of the inner element and the sleeve element; and c) attaching the collar portion of the inner element to the distal end region of the syringe body;

wherein the inner element is at least partially deformable during the mounting process.

When the inner element, which comprises a collar portion and a piercing means protection portion, is attached to the syringe body, the collar portion is slid onto the syringe body. If the syringe body now has a projection or thicker portion, which may serve to lock the collar portion in the axial direction, for example, this can make attachment difficult. As a result of the advantageous slits in the collar portion, however, it is possible to widen the collar portion slightly, making it easier for it to slide onto the syringe body. Widening of this type results in a mechanical load on the predetermined breaking point between the collar portion and the piercing means protection portion. To reduce a mechanical load of this type, it is advantageous for the piercing means protection portion to be slightly deformable. Preferably, in this case the piercing means protection portion is made of a plastics material having thermoplastic properties. The collar portion preferably consists of a plastics material which does not have thermoplastic properties of this type. Thus, the inner element can be heated either before or as it is slid onto the syringe body so that only the piercing means protection portion is slightly deformable. Thus, the inner element can be attached to the syringe body without the predetermined breaking point being subjected to mechanical loading.

Other advantages, aims and expediencies of the present invention are explained on the basis of the following description of the attached drawings. Similar components can have the same reference signs in the various embodiments.

Figure 1:
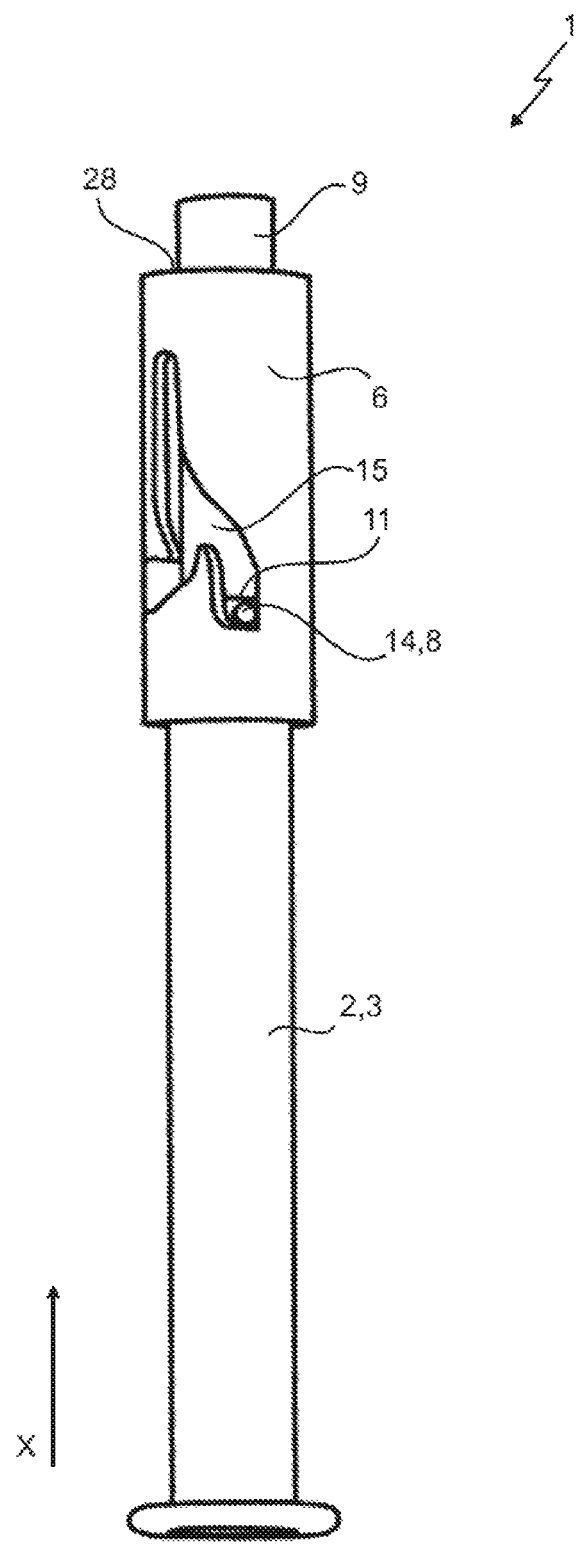
FIG. 1 is an isometric view of a syringe comprising a safety device.
Figure 2:
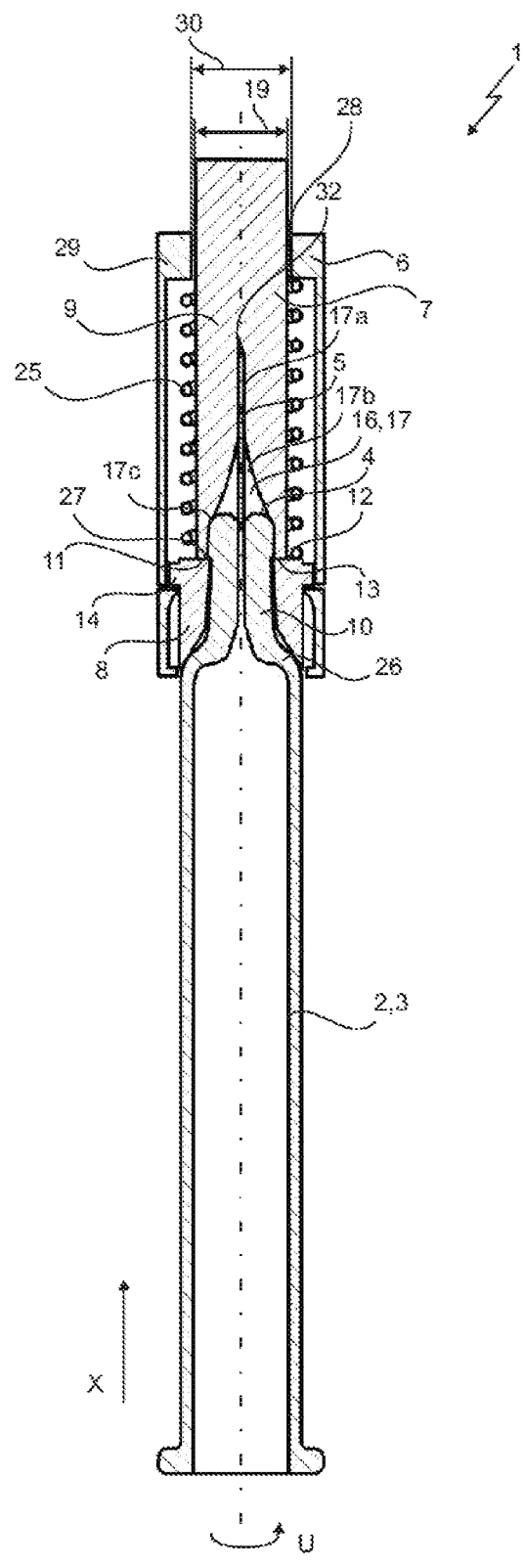
FIG. 2 is a sectional view of a syringe comprising a safety device in accordance with one embodiment.

FIGS. 1 and 2 show a syringe (2) comprising a safety device (1) for avoiding stab wounds, FIG. 1 being an isometric view and FIG. 2 being a sectional view. The syringe (2) comprises a syringe body (3), which is configured as a hollow circular cylinder. The syringe body has a distal end region (10) having a distal end (4). A piercing means (5) is arranged at the distal end (4). This piercing means (5) is connected to the cavity in the syringe body (3) via a hole in the distal end region (10), so that the medium to be injected can pass out of the cavity through the piercing means (5) when the syringe (2) is used. The distal end region (10) is configured as a conical end piece which has a smaller external diameter than the syringe body (3). The syringe furthermore has a transition region (26) in which the external diameter of the syringe body (3) transitions into the external diameter of the end piece. In addition, a projection (27) is arranged on the distal end region.

Furthermore, a safety device (1) for a syringe (2) for avoiding stab wounds is shown, said syringe having a syringe body (3) and a piercing means (5) arranged at the distal end (4) of the syringe body (3). The safety device (1) comprises a sleeve element (6), which extends in an axial direction (X) and encloses the piercing means (5) and the syringe body (3) at least in part, and an inner element (7), at least portions of which are arranged inside the sleeve element (6) and encloses the piercing means (5). The inner element (7) comprises a collar portion (8) and a piercing means protection portion (9) that encloses the piercing means (5), the collar portion (8) being arrangeable on a distal end region (10) of the syringe body (3), the safety device (1) being fastened to the syringe body (3), and the piercing means protection portion (9) being detachable from the collar portion (8) before the syringe (2) is used.

Figure 3:
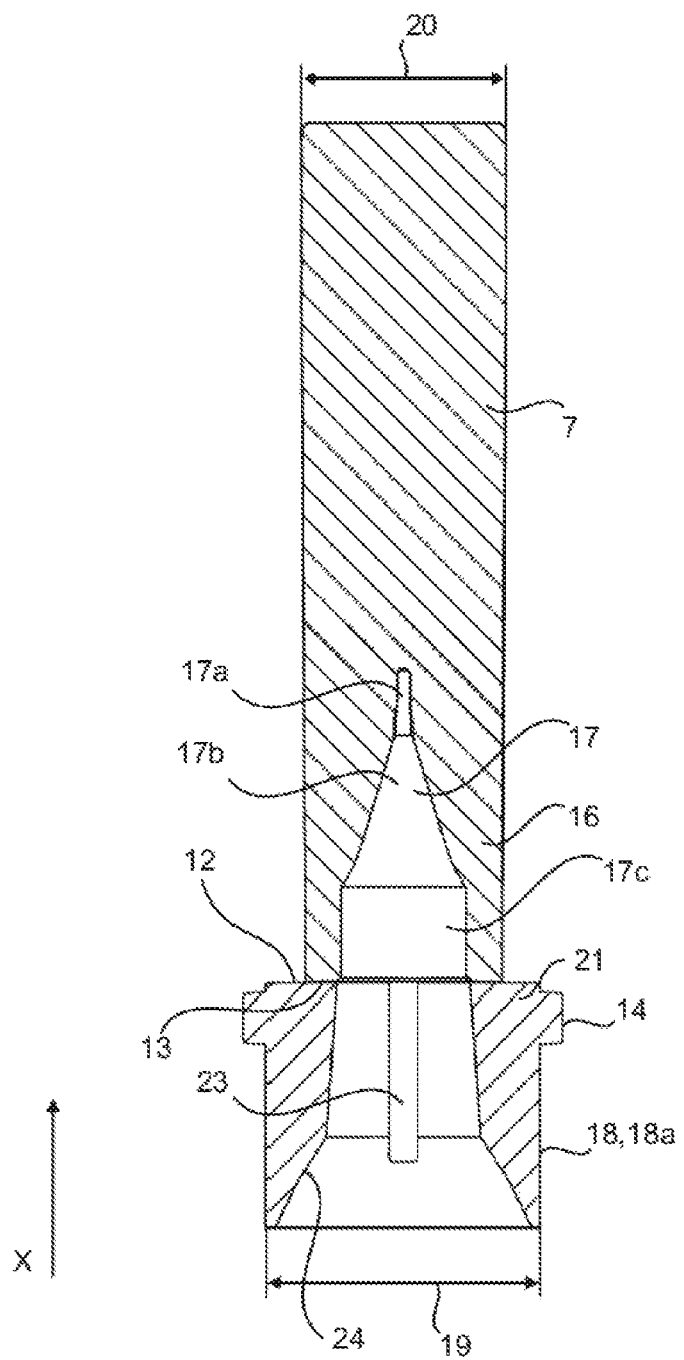
FIG. 3 is a sectional view of the inner element in accordance with one embodiment.
Figure 4:
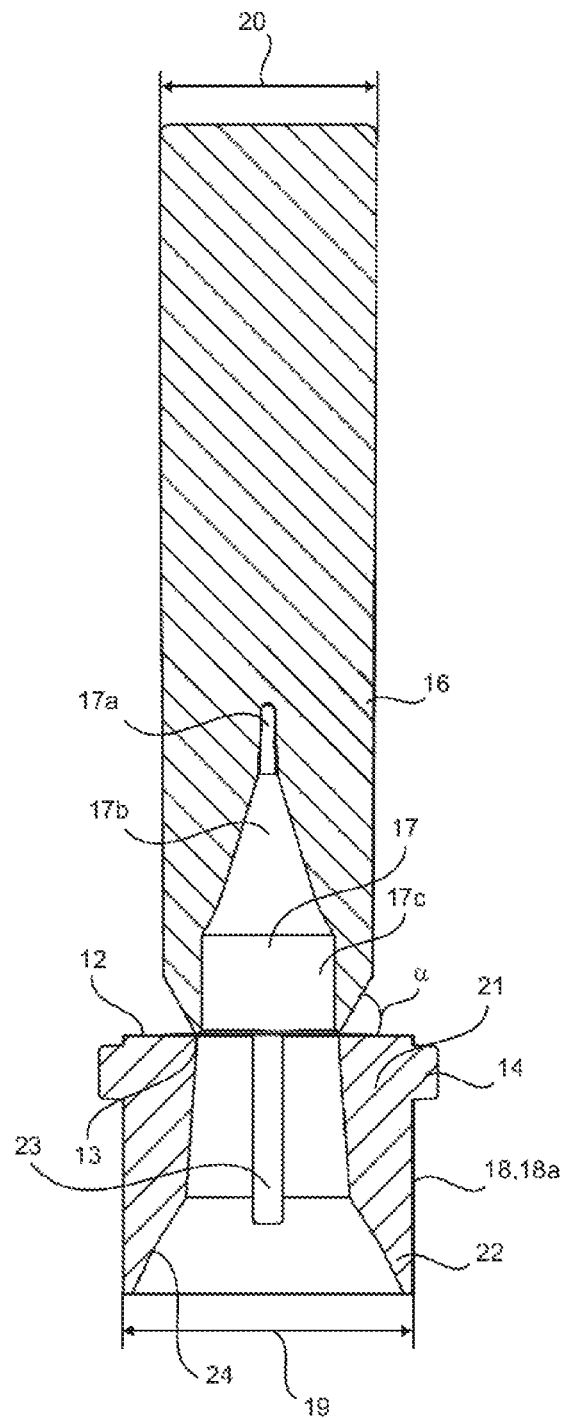
FIG. 4 is a sectional view of the inner element in accordance with a further embodiment.

A predetermined breaking point (11) is arranged between the collar portion (8) and the piercing means protection portion (9). The predetermined breaking point (11) is arranged between a distal end face (12) of the collar portion (8) and a proximal end (13) of the piercing means protection portion (9). Detailed views of the inner element in accordance with two different embodiments are shown in FIGS. 3 and 4. The predetermined breaking point (11) may be a material taper and/or a perforation and/or a notch and/or a crack in the material. For example, FIG. 4 shows a material taper of this type. In this case, in a portion of the proximal end region (16) of the piercing means protection portion (9), the external diameter (19) of the piercing means protection portion (9) tapers in the axial direction (X) towards the collar portion (8). Because the internal diameter of the cavity (17) remains constant in this region, the wall thickness is reduced in this region, creating a predetermined breaking point (11). As a result of the linear decrease in the external diameter (19), the distal end face (12) of the collar portion (8) and an outer face of the piercing means protection portion (9) form an angle α. The angle α is preferably in a range of between 30° and 60°, particularly preferably 45°. FIG. 3 shows a further embodiment of the inner element (7). In this figure, the predetermined breaking point (11) is a perforation and/or a crack in the material.

The collar portion (8) is substantially formed as a hollow circular cylinder (18). The circular cylinder (18) has a lateral surface (18a) on which two guide projections (14) are arranged. The guide projections (14) extend radially outwards away from the lateral surface (18a), and are diametrically opposite one another. Furthermore, said projections are formed as circular cylinders or as pins. These two guide projections (14) are each substantially guided in the axial direction (X) in a guide slot (15) of the sleeve element (6) when the syringe body (3) moves relative to the sleeve element (6). Furthermore, the collar portion (8) is arranged on the distal end region (10) of the syringe body (3) so as to be rotatable in a circumferential direction (U)

The collar portion (8) further comprises a distal region (21) and a proximal region (22). In the distal region, the collar portion (8) has a distal end face (12). A portion of this distal end face abuts a projection (27) or thicker portion at the distal end (4) of the syringe body (3), making locking in the axial direction (X) possible. A further portion of this distal end face (12) forms the predetermined breaking point (11) for the proximal end (13) of the piercing means protection portion (9). Finally, according to one embodiment, a spring element (25) abuts a further portion. The wall of the collar portion (8) further comprises two slits (23) in the distal region (21). The slits (23) extend in the axial direction (X) from the distal end face (12). Slits (23) allow for better adaptation of the collar portion (8) or the inner element (7) to different syringe bodies (3) or easier attachment of the inner element (7) to the syringe body (3). Usually, the inner element (7) is slid over the distal end (4) of the syringe body. This distal end (4) has a projection (27) or thicker portion. As a result of the slits (23), the collar portion (8) can be widened during attachment, meaning that it is easier to slide said collar portion over the projection (27). To prevent mechanical loads on the predetermined breaking point (11), it is advantageous if the piercing means protection portion (9) is at least slightly deformable during the attachment of the inner element (7) to the syringe body (3). The collar portion (8) further has an inside taper (24) in the proximal region (22) thereof. This inside taper (24) abuts the transition region (26) of the syringe body (3) and thus serves as a second bearing point.

The distal end (32) and a connecting distal region of the piercing means (5) are arranged in a cavity (17) in a proximal end region (16) of the piercing means protection portion (9). The cavity comprises a first region (17a), the piercing means (5) abutting the internal walls thereof in this first region. Advantageously, an inner part made of a resilient material, for example rubber or a synthetic elastomer, may be arranged in the cavity (17) of the piercing means protection portion (9). The piercing means (5) or the polished surface of the piercing means would thus be protected against damage caused by mechanical influences. In a third region (17c), the cavity (17) further extends over the distal end (4) or part of the distal end region (10) of the syringe body (3). Between the first (17a) and the third (17c) region there is a second region (17b), in which the internal diameter of the cavity (17) increases from the first region (17a) up to the third region (17c). Advantageously, the inner wall of the piercing means protection portion or the inner part sealingly abuts the distal end (4) of the syringe body (3) in the third region (17c). The piercing means (5) is thus protected from contamination.

FIG. 2 further shows a safety device (1), which has a spring element (25) in the form of a spiral spring which is operatively connected to the syringe body (3) and counteracts the movement of the sleeve element (6) relative to the safety device (1). The inner element (7) is arranged inside the sleeve element (6). In this case, the spring element encloses the piercing means protection portion (9). The external diameter (19) of the collar portion (8) is greater than the external diameter (20) of the piercing means protection portion (9). The spring element (25) thus abuts a distal end face (12) of the collar portion (8) on one side and a wall region (29) which delimits the distal opening (28) in the sleeve element (6) on the other side. Furthermore, the external diameter (19) of the piercing means protection portion (9) is smaller than the internal diameter (30) of the distal opening (28) in the sleeve element (6). The piercing means protection portion (9) extends through the distal opening (28) and thus protrudes beyond the sleeve element. The region protruding beyond the sleeve element serves as a handle region (31), by means of which a rotatory or pulling force can be exerted on the inner element (7) or predetermined breaking point (11). It would be conceivable to configure the surface of the inner element (7) in this handle region (31) to have an anti-slip effect. Said effect could be brought about, for example, by way of an appropriate coating or a roughened surface.

After the predetermined breaking point is broken apart, for example by way of a rotary or pulling movement, and the piercing means protection portion (9) has been removed, the piercing means (5) remains inside the sleeve element (6) until the intended use. During use, the distal end of the syringe (2) or safety device (1) is pressed against the patient's skin. During use, the sleeve element (6) is displaced counter to the spring force of the spring element (25), so that the piercing means (5) can pass through the distal opening (28) in the sleeve element (6). The sleeve element (6) is slid over the distal end region (10) of the syringe body (3) in this case. As a result of the guidance of the guide projection (14) in the guide slot (15), the collar portion (8) rotates in the circumferential direction (U). After the syringe (2) has been used, the sleeve element (6), driven by the spring force of the spring element (25), automatically slides back over the piercing means (5). As a result of the guidance of the guide projections (14) in the guide slot (15), the collar portion (8) rotates counter to the circumferential direction (U). The user is thus protected against stab wounds from the used and contaminated piercing means.

All of the features disclosed in the application documents are claimed to be essential to the invention provided that they are novel over the prior art, either on their own or in combination with one another.

LIST OF REFERENCE NUMERALS

1 Safety device
2 Syringe
3 Syringe body
4 Distal end of the syringe body
5 Piercing means
6 Sleeve element
7 Inner element
8 Collar portion
9 Piercing means protection portion
10 Distal end region
11 Predetermined breaking point
12 Distal end face of the collar portion
13 Proximal end of the piercing means protection portion
14 Guide projection
15 Guide slot
16 Proximal end region of the piercing means protection portion
17 Cavity
17a First region of the cavity
17b Second region of the cavity
17c Third region of the cavity
18 Circular cylinder
18a Lateral surface of the circular cylinder
19 External diameter of the collar portion
20 External diameter of the piercing means protection portion
21 Distal region of the collar portion
22 Proximal region of the collar portion
23 Slit
24 Inside taper
25 Spring element
26 Transition region
27 Projection
28 Distal opening of the sleeve element
29 Wall region
30 Internal diameter
31 Handle region
32 Distal end of the piercing means
X Axial direction
U Circumferential direction

The invention claimed is:

1. A safety device for a syringe for avoiding stab wounds, said syringe having a syringe body and a piercing means arranged at the distal end of the syringe body, said safety device comprising a sleeve element which extends in an axial direction (X) and encloses the piercing means and the syringe body at least in part, and an inner element, at least portions of which are arranged inside the sleeve element and enclose the piercing means, wherein:

the inner element comprises a collar portion and a piercing means protection portion that encloses the piercing means, the collar portion being arranged on a distal end region of the syringe body such that the collar portion can rotate in a circumferential direction (U) and fasten the safety device to the syringe body, and a predetermined breaking point being arranged between the collar portion and the piercing means protection portion, as a result of which the piercing means protection portion can be detached from the collar portion before the syringe is used, and wherein the collar portion has at least one guide projection which engages in at least one guide slot of the sleeve element, the guide projection being substantially guided in the axial direction (X) in the at least one guide slot of the sleeve element when the syringe body moves relative to the sleeve element.

2. The safety device according to claim 1, wherein:
the predetermined breaking point is arranged between a distal end face of the collar portion and a proximal end of the piercing means protection portion, the predetermined breaking point being a material taper and/or a perforation and/or a notch and/or a score in the material.

3. The safety device according to claim 1, wherein:
the piercing means protection portion has a cavity in a proximal end region, the piercing means and portions of the distal end region of the syringe body being arrangeable in the cavity.

4. The safety device according to claim 3, wherein:
an inner part made of a resilient material is arranged in the cavity in the piercing means protection portion, the resilient material being rubber or a synthetic elastomer.

5. The safety device according to claim 1, wherein:
the collar portion is substantially formed as a hollow circular cylinder, the circular cylinder having a lateral surface on which the at least one guide projection is arranged, an external diameter of the collar portion being greater than an external diameter of the piercing means protection portion.

6. The safety device according to claim 1, wherein:
the collar portion comprises a distal region and a proximal region, in the distal region the wall of the collar portion having at least two slits which extend in the axial direction (X), and the proximal region having an inside taper.

7. The safety device according to claim 1, wherein:
the safety device has at least one spring element, which is operatively connected to the syringe body and counteracts the movement of the syringe body relative to the sleeve element.

8. The safety device according to claim 1, wherein:
the collar portion and the piercing means protection portion are made of different materials.

9. The safety device according to claim 1, wherein:
the piercing means protection portion is made of a thermoplastic elastomer (TPE) and the collar portion is made of polyoxymethylene (POM).

10. A method for mounting the safety device according to claim 1 and for arranging the safety device on a syringe body, the method comprising the steps of:
a) inserting the spring element into the interior of the sleeve element in the axial direction (X);
b) inserting the inner element into the interior of the sleeve element in the axial direction (X) such that the spring element is arranged between the collar portion of the inner element and the sleeve element; and
c) attaching the collar portion of the inner element to the distal end region of the syringe body;
wherein the inner element is heated during the mounting process so as to be at least partially deformable.

11. A safety device for a syringe for avoiding stab wounds, said syringe having a syringe body and a piercing means arranged at the distal end of the syringe body, said safety device comprising a sleeve element which extends in an axial direction (X) and encloses the piercing means and the syringe body at least in part, and an inner element, at least portions of which are arranged inside the sleeve element and enclose the piercing means, wherein:
the inner element comprises a collar portion and a piercing means protection portion that encloses the piercing means, the collar portion being arranged on a distal end region of the syringe body such that the collar portion can rotate in a circumferential direction (U) and fasten the safety device to the syringe body, and a predetermined breaking point being arranged between the collar portion and the piercing means protection portion, as a result of which the piercing means protection portion can be detached from the collar portion before the syringe is used, and wherein the safety device has at least one spring element, which is operatively connected to the syringe body and counteracts the movement of the syringe body relative to the sleeve element.

12. The safety device according to claim 11, wherein: the predetermined breaking point is arranged between a distal end face of the collar portion and a proximal end of the piercing means protection portion, the predetermined breaking point being a material taper and/or a perforation and/or a notch and/or a score in the material.

13. The safety device according to claim 11, wherein: the piercing means protection portion has a cavity in a proximal end region, the piercing means and portions of the distal end region of the syringe body being arrangeable in the cavity.

14. The safety device according to claim 13, wherein: an inner part made of a resilient material is arranged in the cavity in the piercing means protection portion, the resilient material being rubber or a synthetic elastomer.

15. The safety device according to claim 11, wherein: the collar portion comprises a distal region and a proximal region, in the distal region the wall of the collar portion having at least two slits which extend in the axial direction (X), and the proximal region having an inside taper.

16. A safety device for a syringe for avoiding stab wounds, said syringe having a syringe body and a piercing means arranged at the distal end of the syringe body, said safety device comprising a sleeve element which extends in an axial direction (X) and encloses the piercing means and the syringe body at least in part, and an inner element, at least portions of which are arranged inside the sleeve element and enclose the piercing means, wherein:
the inner element comprises a collar portion and a piercing means protection portion that encloses the piercing means, the collar portion being arranged on a distal end region of the syringe body such that the collar portion can rotate in a circumferential direction (U) and fasten the safety device to the syringe body, and a predetermined breaking point being arranged between the collar portion and the piercing means protection portion, as a result of which the piercing means protection portion can be detached from the collar portion before the syringe is used, and wherein the collar portion comprises a distal region and a proximal region, in the distal region the wall of the collar portion having at least two slits which extend in the axial direction (X), and the proximal region having an inside taper.

17. The safety device according to claim 16, wherein: the predetermined breaking point is arranged between a distal end face of the collar portion and a proximal end of the piercing means protection portion, the predetermined breaking point being a material taper and/or a perforation and/or a notch and/or a score in the material.

18. The safety device according to claim 16, wherein: the piercing means protection portion has a cavity in a proximal end region, the piercing means and portions of the distal end region of the syringe body being arrangeable in the cavity.

19. The safety device according to claim 16, wherein: an inner part made of a resilient material is arranged in the cavity in the piercing means protection portion, the resilient material being rubber or a synthetic elastomer.

\* \* \* \* \*